United States Patent [19]

Hussmann et al.

[11] Patent Number: 4,929,761
[45] Date of Patent: May 29, 1990

[54] PREPARATION OF SUBSTITUTED BENZOPHENONES

[75] Inventors: Gregory P. Hussmann, Warrenville; Carl A. Udovich, Joliet, both of Ill.

[73] Assignee: Amoco Corporation, Chicago, Ill.

[21] Appl. No.: 944,515

[22] Filed: Dec. 22, 1986

[51] Int. Cl.$^5$ .............................................. C07C 45/48
[52] U.S. Cl. .................................................... 568/319
[58] Field of Search ........................ 568/319, 397, 398

[56] References Cited

U.S. PATENT DOCUMENTS 2,811,559 10/1957 Chesrown et al. .................. 568/397

FOREIGN PATENT DOCUMENTS

| 660910 | 3/1964 | Italy | 568/319 |
| 61-207354 | 9/1986 | Japan | 568/319 |
| 615543 | 1/1946 | United Kingdom | 568/319 |

OTHER PUBLICATIONS

Imanaka et al., Chem. Abst., vol. 81, #37016h, (1974).
Sosnina et al. (I), Chem. Abst., vol. 71, #140,407k, (1971).
Sosnina et al. (II), Chem. Abst., vol. 71, #41654n, (1971).

Primary Examiner—James H. Reamer
Attorney, Agent, or Firm—Gunar J. Blumberg; William H. Magidson; Ralph C. Medhurst

[57] ABSTRACT

There is disclosed a process for the preparation of a benzophenone, which process comprises contacting a feed comprising an aromatic carboxylic acid in the vapor phase and under suitable conditions with a catalyst which is capable of catalyzing the conversion of an aromatic carboxylic acid to a benzophenone to provide a yield of at least 10% benzophenone and which comprises at least one oxide that is an oxide of an element having an atomic number of at least 60. Typical catalysts are neodymium trioxide and a mixture of thorium dioxide and magnesium oxide.

6 Claims, 1 Drawing Sheet

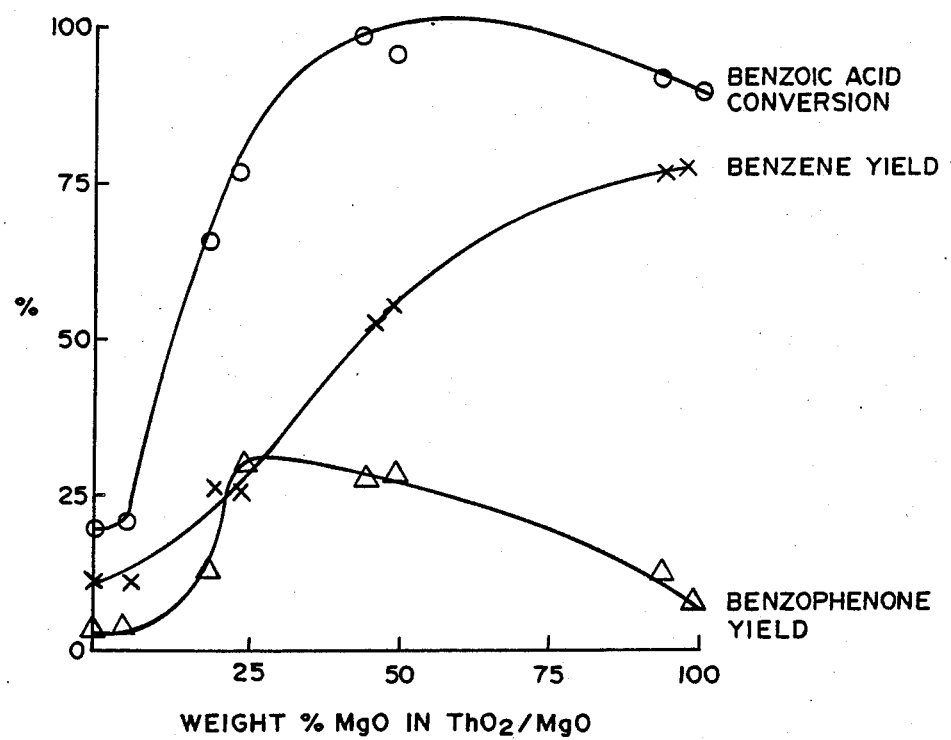

PREPARATION OF SUBSTITUTED BENZOPHENONES

CROSS-REFERENCE TO RELATED APPLICATIONS

This application is being filed concurrently in the U.S. Patent and Trademark Office with U.S. Ser. No. 944,517, which is directed to the preparation of dialkyl ketones by the ketonic decarboxylative coupling of aliphatic carboxylic acids in the presence of a catalyst comprising manganese dioxide on a support of catalytically active alumina.

In addition, this application is being filed concurrently in the U.S. Patent and Trademark Office with U.S. Ser. No. 944,516, which is directed to the preparation of substituted benzophenones by the ketonic decarboxylative coupling of 3-cyclohexene carboxylic acids and subsequent dehydrogenation.

BACKGROUND OF THE INVENTION

1. Field of the Invention

The present invention relates to a method or process for preparing aromatic ketones by a ketonic decarboxylative coupling of aromatic carboxylic acids. More particularly, the present invention relates to a process for preparing benzophenones by means of a gas-phase or vapor-phase coupling of aromatic carboxylic acids.

2. Description of the Prior Art

It has been shown that ketones can be formed by means of ketonic decarboxylation of carboxylic acids. For example, in an article in ZH. OBSHCH. KHIM., 30, 9, 2789 (1960), Rubinshtein et al., discussed the use of $ThO_2$, $CeO_2$, $CaCO_3$, $BaCO_3$, $ZnO_2$, and CdO as active catalysts for ketonization and the vapor-phase catalytic ketonization of acetic acid over carbonates of alkaline earth metals (Ca, Ba, Sr, and Mg). In KINET. KATAL., 2, 2, 172 (1961), Yakerson et al., investigated the kinetics of the thermal decomposition of lithium, sodium, and barium acetate to ketone and used the data to specify the mechanism of the vapor-phase ketonization of acetic acid and its decomposition to methane. In KINET. KATAL., 2, 6, 907 (1961), Yakerson et al., discussed the kinetics of vapor-phase catalytic ketonization of acetic acid over $TiO_2$, $ZrO_2$, $SnO_2$, $CeO_2$, and BeO. In IZV. AKAD. NAUK SSSR, No. 1, 83 (1966), Yakerson et al., discussed the catalytic ketonization of acetic acid over a mixed binary catalyst system of $ZrO_2$-$Al_2O_3$. In ZH. PRIKL. KHIM., 50, 2126 (1977), Shmelev et al., reported that diethyl ketone could be prepared by the ketonization of propionic acid in the presence of a catalyst of manganese dioxide supported on silica gel.

Furthermore, in Japanese Published patent application Kokai No. Sho 57(1982)-197237, Matsuoka disclosed a method for preparing ketones from straight-chain or branched aliphatic carboxylic acids by employing a gas-phase contact reaction whereby an aliphatic carboxylic acid is contacted with a catalyst comprising zirconium oxide and, optionally, a support of alumina or silica gel. In this Japanese patent publication, he also listed conventionally-used catalysts for the synthesis of a molecule of ketone from two molecules of a carboxylic acid as being calcium oxide, barium oxide, lithium oxide, alumina, chromium oxide, manganese oxide, thorium oxide, gallium oxide, indium oxide, and oxides of rare earth elements and mentioned that such catalysts provide low conversions and selectivities.

In U.S. Pat. No. 4,014,889, Schreckenberg et al., disclosed the preparation of a ketone by means of the reaction of an aromatic or heterocyclic aldehyde in the presence of a cyanide ion with an unsaturated compound having the formula:

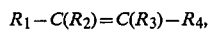

$$R_1-C(R_2)=C(R_3)-R_4,$$

"$R_1$," "$R_2$," and "$R_3$" are the same or different and are selected from the group of hydrogen, optionally substituted aliphatic, cycloaliphatic, araliphatic, aromatic, heterocyclic and carboxylic ester and "$R_4$" is nitrile, —CO—$R_5$ or —CO—O$R_5$ wherein "$R_5$" is selected from the group of optionally substituted aliphatic, cycloaliphatic, araliphatic, aromatic, and heterocyclic and "$R_1$" and "$R_2$" and/or "$R_1$" and "$R_3$" and/or "$R_2$" and "$R_5$" or "$R_3$" and "$R_5$" together with the carbon atoms to which they are attached as substituents can also form a carbocyclic or heterocyclic ring.

In U.S. Pat. No. 3,479,400, Lese et al., disclosed a process for converting a 1,1-diarylalkane to the corresponding diaryl ketone, which process involves oxidizing the 1,1-diarylalkane in a first reaction zone with nitric acid, reacting the solid product from the first reaction zone with nitric acid in a second reaction zone under conditions that are more severe than those employed in the first reaction zone to obtain the desired diaryl ketone and optionally recycling an aqueous solution containing nitric acid to the first reaction zone.

In U.S. Pat. No. 4,007,211, Trost et al., disclosed a method for converting an alpha-thiocarboxylic acid compound to the corresponding ketone. In this method, the carboxylic acid or its ester is first subjected to a sulfenylation reaction for positioning an "—SR" group alpha to the carboxylic acid group and then the sulfenylated product is subjected to oxidative decarboxylation in the presence of an alkali metal periodate or a halogen source.

It has now been found that aromatic ketones, such as benzophenones, can be prepared in improved yields by the ketonic decarboxylative coupling of aromatic carboxylic acids.

SUMMARY OF THE INVENTION

There is disclosed a process for preparing an aromatic ketone, such as a benzophenone, from an aromatic carboxylic acid, which process comprises contacting a feed comprising said carboxylic acid in the vapor phase and under suitable conditions with a catalyst which is capable of catalyzing the conversion of an aromatic carboxylic acid to a benzophenone to provide a yield of at least 10% benzophenone and which comprises at least one oxide that is an oxide of an element having an atomic number of at least 60. Catalysts that are suitable are a catalyst comprising neodymium trioxide and a catalyst comprising a mixture of thorium dioxide and magnesium oxide. The latter catalyst can have a magnesium oxide content within the range of about 21 wt. % to about 75 wt. % magnesium oxide. A typical feed is benzoic acid.

BRIEF DESCRIPTION OF THE DRAWING

The accompanying FIGURE presents the effect of the amount of magnesium oxide in a catalyst comprising a mixture of thorium dioxide and magnesium oxide upon the conversion of benzoic acid, the yield of benzene, and the yield of benzophenone, when such catalyst is being employed to convert benzoic acid to benzophenone.

DETAILED DESCRIPTION OF THE INVENTION

According to the present invention, there is provided a process for preparing a benzophenone by means of the ketonic decarboxylative coupling of an aromatic carboxylic acid. More particularly, there is provided a process for preparing an aromatic ketone, such as a benzophenone, by means of the ketonic decarboxylative coupling of an aromatic carboxylic acid, such as a benzoic acid. The coupling of the aromatic carboxylic acids provides improved yields of the desired benzophenones. Hence, the feedstock for this process can be a feed containing one or more aromatic carboxylic acids. The feedstock can comprise benzoic acid, p-hydroxybenzoic acid, or trimellitic anhydride. Benzophenone can be obtained from benzoic acid; 4,4'-dihydroxybenzophenone, from p-hydroxybenzoic acid; and benzophenone dianhydride, from trimellitic anhydride.

According to the present invention, there is provided a process for preparing a benzophenone from an aromatic carboxylic acid, which process comprises contacting a feed comprising said carboxylic acid in the vapor phase and under suitable conditions with a catalyst which is capable of catalyzing the conversion of an aromatic carboxylic acid to a benzophenone and which comprises at least one oxide that is an oxide of an element having an atomic number of at least 60.

Therefore, the catalyst that is employed in the process of the present invention is a catalyst which comprises at least one oxide that is an oxide of an element of the Periodic Table having an atomic number of at least 60 and which is capable of catalyzing the conversion of an aromatic carboxylic acid to a benzophenone to provide a yield of at least 10% benzophenone. Two catalytic compositions which meet the above requirements are (1) a catalyst which comprises an oxide of neodymium (atomic number of 60), $Nd_2O_3$, and (2) a catalyst which comprises a mixture of an oxide of thorium (atomic number of 90), $ThO_2$, and an oxide of magnesium, MgO.

These catalysts can be prepared by compressing the finely-divided material into shaped particles, such as pellets. In the case of the mixed oxide catalyst, granulated particles of the thorium dioxide and magnesium oxide can be physically mixed in the desired proportion.

Optionally, the catalyst can also comprise a suitable support material. Typical support materials are titania, silica, silica-alumina, and catalytically active alumina. Materials such as glass wool could be used. Catalytically active alumina is a preferred support material. Such alumina is readily accessible from catalyst manufacturers and catalyst vendors and should have a surface area within the range of about 5 $m^2$/gm to about 400 $m^2$/gm. Preferably, the surface area is in the range of about 50 $m^2$/gm to about 250 $m^2$/gm.

The catalyst can be prepared conveniently by impregnating a support, if such support is being used, with a solution of a heat-decomposable compound of the particular element being applied to the support material. Such impregnation can be performed by the incipient wetness technique, which involves employing just enough of the solution to fill the pores of the material that is being impregnated. The impregnated material is then calcined after drying. Drying can be carried out at a temperature within the range of about 100° C. to about 149° C., or higher, for a period of time within the range of about 1 hr to about 16 hr, while the calcination can be performed in air at a temperature within the range of about 454° C. to about 593° C., or higher, for a period of time within the range of about 0.5 hr to about 2 hr. If the supported thorium dioxide-magnesium oxide catalyst is being prepared, solutions of the heat-decomposable compounds of thorium and magnesium are employed to impregnate the selected support. Alternatively, one solution containing compounds of both elements can be used.

The finished supported catalyst should contain the oxide of the particular metal in an amount within the range of about 5 wt. % to about 40 wt. %. In the case of neodymium trioxide, the catalyst contains neodymium trioxide within the range of about 5 wt. % to about 40 wt. %, based upon the total weight of the catalyst. Preferably, the catalyst contains neodymium trioxide within the range of about 15 wt. % to about 25 wt. %. In the case of the supported thorium dioxide-magnesium oxide catalyst, the catalyst should contain the two oxides in a total amount within the range of about 15 wt. % to about 40 wt. %, based upon the weight of the catalyst, preferably, within the range of about 15 wt. % to about 25 wt. %. Furthermore, the proportion of magnesium oxide in the mixed oxides should be maintained within the range of about 21 wt. % to about 75 wt. % magnesium oxide, preferably within the range of about 22 wt. % to about 60 wt. % magnesium oxide, based upon the sum of the weights of the thorium dioxide and magnesium oxide. The values of these ranges are discussed hereinbelow in Examples 12 through 19 and are presented in the accompanying FIGURE.

According to the process of the present invention, the feed to be treated is contacted with the catalyst in a gas phase or vapor phase and under suitable conditions. Typical suitable conditions comprise a temperature within the range of about 250° C. to about 500° C., a pressure within the range of about 5 psia to about 200 psia, and a contact time within the range of about 1 sec to about 10 sec. Preferred conditions comprise a temperature within the range of about 325° C. to about 400° C., a pressure within the range of about 5 psia to about 35 psia, and a contact time within the range of about 3 sec to about 5 sec.

The catalysts of the process of the present invention will become deactivated after a time because of an accumulation of coke (carbonaceous deposits). When deactivation does occur, the deactivation catalyst can be regenerated by means of heating it in air or an oxygen-containing gas at a temperature and for a period of time that are sufficient for burning off the coke.

It is of interest to note that aromatic carboxylic acids which contain strong electron-donating groups, such as para-hydroxy benzoic acid, or strong electron withdrawing groups, such as para-nitro benzoic acid, do not yield appreciable quantities of an expected ketone coupling product. In general, such aromatic acids will undergo extensive decarboxylation. It is to be understood that aromatic acid ketonic decarboxylative coupling competes with the decarboxylation reaction and, consequently, low yields are often obtained. The process of the present invention provides benzophenones in improved yields, i.e., moderate to good yields. Consequently, the process provides an improved method for preparing benzophenones from aromatic carboxylic acids.

While it is not intended to be limited by the following theory, it is postulated that gas-phase ketonic decarboxylative coupling occurs through the intermediacy of a metal carboxylate salt which decomposes in a carbanionic or radical fashion to the observed products.

The following examples are being presented to facilitate the understanding of the present invention. It is to be understood that these examples are presented for the purpose of illustration only and are not intended to limit the scope of the present invention.

All tests that were conducted in the following examples were performed in the gas phase in a simple tube furnace reactor. Typically, a 5-ml portion of a 14/42-mesh catalyst material was charged into a quartz reactor, which was then placed in a single zone 12-inch Lindburg furnace controlled by a Eurotherm 919 system. In each of these examples, 2.2 molar benzoic acid in tetrahydrofuran solution was added at a rate of about 0.10 ml/min by means of a Harvard Apparatus syringe drive. Of course, solid reactants were necessarily dissolved in an inert solvent, such as toluene, prior to addition. Throughout the reaction, a 10 ml/min flow of nitrogen was swept through the reactor and the catalyst bed. The effluent from the reactor was collected in an ice-cooled receiving flask and analyzed by gas chromatography or liquid chromatography. Reaction products were identified by gas chromatography-mass spectroscopy or by comparison of retention time with that of an authentic sample. Quantitative analysis was performed by gas chromatography using internal standards and predetermined response factors.

The benzophenone materials produced by the process of the present invention are useful heat transfer agents and can be converted to useful monomers.

EXAMPLE 1-11

The coupling of benzoic acid in the presence of various catalysts was attempted in these examples. The catalysts and the temperatures employed are listed hereinbelow in Table I, along with the product distribution obtained in each test. The product distribution was calculated directly from percent gas chromatographic area.

TABLE I

Coupling of Benzoic Acid

| Ex. | Catalyst | Temp. (°C.) | % Product Distribution | | | |
|---|---|---|---|---|---|---|
| | | | Benzoic Acid | Benzophenone | Benzene | Other Products |
| 1 | CaO[a] | 450 | 0 | 3 | 91 | — |
| 2 | MgO[a] | 425 | 41 | 19 | 36 | — |
| 3 | 2% MgO/SiO$_2$ | 425 | 52 | — | 4 | 39 |
| 4 | SiO$_2$ | 425 | 53 | — | 13 | 27 |
| 5 | Fe$_2$O$_3$ | 425 | 26 | 2 | 43 | 17 |
| 6 | ZrO$_2$ | 425 | 91 | 0 | 3 | — |
| 7 | 19% MnO$_2$/Al$_2$O$_3$ | 420 | 53 | 2 | 3 | 2 |
| 8 | Nd$_2$O$_3$ | 480 | 0 | 38 | 49 | — |
| 9 | ThO$_2$ | 450 | 80 | 3 | 14 | — |
| 10 | ThO$_2$/MgO (3:1) | 450 | 26 | 28 | 27 | — |
| 11 | ThO$_2$/MgO/SiO$_2$ | 425 | 45 | 1 | 4 | 47 |

[a]Considerable coking occurred.

The best yields of benzophenone were attained with the use of a catalyst of neodymium oxide or a catalyst comprising thorium oxide combined with magnesium oxide in a weight ratio of 3:1, i.e., 25 wt. % magnesium oxide.

EXAMPLES 12-19

In each of these examples, a catalyst containing a different weight ratio of thorium dioxide to magnesium oxide was used to convert benzoic acid to benzophenone. In each case, a temperature of 450° C. and contact time within the range of 3 sec to 4 sec were maintained. The results of these tests are presented in the accompanying FIGURE. These results demonstrate that a catalyst comprising thorium dioxide and magnesium oxide should contain magnesium oxide in an amount within the range of about 21.5 wt. % to about 75 wt. % magnesium oxide, based upon the sum of the weights of the thorium dioxide and magnesium oxide, to provide a yield of at least 20% benzophenone. If the catalyst contains magnesium oxide in an amount within the range of about 22 wt. % to about 60 wt. %, it will furnish a benzophenone yield of at least 25%. A catalyst containing about 25 wt. % magnesium oxide will provide the best benzophenone yield, approximately 32%.

The results presented hereinabove clearly demonstrate that at least moderate yields of benzophenones can be obtained when contacting aromatic carboxylic acids with catalysts comprising neodymium trioxide or a mixture of thorium dioxide and magnesium oxide in selected ratios.

What is claimed is:

1. A process for preparing a benzophenone from an aromatic carboxylic acid, which process comprises contacting a feed comprising said aromatic carboxylic acid in the vapor phase and at a temperature within the range of from about 250° C. to about 500° C., a pressure within the range of from about 5 psia to about 200 psia and a contact time within the range of about 1 sec to 10 sec with a catalyst selected from the group consisting essentially of Nd$_2$O$_3$ and ThO$_2$/MgO, said MgO in an amount within the range of about 21.5 wt. % to about 75 wt. %, based on sum of weights of ThO$_2$ and MgO, to convert said aromatic carboxylic acid to a benzophenone.

2. The process of claim 1, wherein said catalyst is neodymium trioxide upon a support of catalytically active alumina, said neodymium trioxide being present in an amount within the range of from about 5 wt. % to about 40 wt. %, based on total weight of the catalyst.

3. The process of claim 1, wherein said catalyst is a mixture of thorium dioxide and magnesium oxide upon a support of catalytically active alumina, said mixture containing the two oxides in a total amount within the range of from about 15 wt. % to about 40 wt. %, based on the weight of the catalyst.

4. The process of claim 1, wherein said magnesium oxide is present in said mixture in an amount that is within the range of about 22 wt. % to about 60 wt. % magnesium oxide, based upon the weight of said mixture.

5. The process of claim 4, wherein said magnesium oxide is present in said mixture in an amount of about 25 wt. %, based upon the weight of said mixture.

6. The process of claim 1 wherein said aromatic carboxylic acid is benzoic acid.

* * * * *